United States Patent [19]
Szycher et al.

[11] Patent Number: 5,254,662
[45] Date of Patent: Oct. 19, 1993

[54] BIOSTABLE POLYURETHANE PRODUCTS

[75] Inventors: Michael Szycher, Lynnfield, Mass.; Andrew M. Reed, Arvada, Colo.

[73] Assignee: PolyMedia Industries, Inc., Burlington, Mass.

[21] Appl. No.: 885,927

[22] Filed: May 18, 1992

Related U.S. Application Data

[63] Continuation of Ser. No. 581,013, Sep. 12, 1990.

[51] Int. Cl.$^5$ .................. C08G 18/42; C08G 18/44
[52] U.S. Cl. .......................... 528/67; 528/85; 623/1; 623/8; 623/11
[58] Field of Search ............ 528/67, 85; 623/1, 8, 623/11

[56] References Cited
U.S. PATENT DOCUMENTS 4,160,853  7/1979  Ammons .................. 428/425
5,133,742  7/1992  Pinchuk .................... 528/44

Primary Examiner—John Kight, III
Assistant Examiner—Rachel Johnson
Attorney, Agent, or Firm—Morgan & Finnegan

[57] ABSTRACT

Polyurethane products having long-term biostability in combination with a low modulus of elasticity and a high ultimate tensile strength and other desireable mechanical properties which are particularly useful as leads for implantable pacemakers, as vascular grafts, as mammary prostheses, and as other products which are intended to be placed within the body of a mammal for extended periods with no substantial degradation of the product. The polyurethanes are prepared from the reaction of an organic diisocyanate, preferably an aliphatic or cycloaliphatic diisocyanate with polycarbonate glycol chained extended with diol, diamine or a mixture of diamine and alkanolamine.

25 Claims, No Drawings

BIOSTABLE POLYURETHANE PRODUCTS

This is a continuation of application Ser. No. 07/581,013, filed on Sep. 12, 1990, now abandoned.

BACKGROUND OF THE INVENTION

This invention relates to polyurethane polymers having a combination of specific properties that makes these polymers especially suitable for long term implantation within a living body. The biostable polymers of this invention possess, inter alia, a low modulus of elasticity and a high ultimate tensile strength as well as the biostability to permit them to be implanted within a living body and exhibit little or no degradation over extended periods.

Extensive investigations have been undertaken over many years to find materials that will be biologically and chemically stable towards body fluids and body tissue. This area of research has become increasingly important with the development of various objects and articles which can be implanted within a living body, such as pacemaker leads, vascular grafts, mammary prostheses, pacemaker bodies, probes, cannulas, catheters, and the like.

Polyurethanes have become particularly crucial in the production of pacemaker leads which provide the pathway for the pacemaker energy output into the heart. The lead insulation may be the most simple looking part of the device, but is one of the most critical components. While it is not unreasonable for a patient to require replacements of the pacemaker energy supply units during his/her life, the insertion of the lead is the more critical portion of the operation and thus must be expected to remain unchanged and provide absolute reliability for periods of 15 years or longer. Unfortunately, the currently available pacemaker leads are known to biodegrade. The biodegradation is characterized by surface fissuring caused by oxidation of the conventional ether linkages present within the polyurethane molecular chain. The oxidation leads to chain cleavage, reduction in molecular weight and eventual catastrophic mechanical failure. Surface fissuring is a progressive phenomenon which starts as surface microfissures which continue to propagate into the bulk, eventually resulting in loss of electrical insulating capacity and inappropriate heart muscle stimulation. The development of a polyurethane polymer in which the onset of microscopic surface fissuring is substantially delayed and/or prevented is desirable to develop improved pacemaker leads.

Vascular grafts, particularly arterial grafts having diameters of 4 mm or less and suitable for the replacement of coronary arteries, represent a further potential large market for polyurethane polymers if only a suitable material existed. It is generally accepted that dacron and polytetrafluoroethylene grafts, while having sufficient tensile strength to be suitable for use in large and medium diameter grafts, fail when used as small diameter grafts due to their excessive stiffness, i.e. they do not exhibit a sufficiently low elastic modulus. Most currently available polyurethanes, as well as being biodegradable, suffer from a similar problem in that when they have good tensile strengths of about 4500 psi they also have high moduli. There is thus a need for a biostable polyurethane polymer which has both a high tensile strength and a low elastic modulus and which can be formed into a small diameter vascular graft.

Mammary prostheses today are generally made of a silicone bag containing a silicone gel. In many cases, after a few years, the tissue surrounding these implants stiffens, necessitating surgical removal. One effort to overcome this problem is to wrap a polyurethane foam around the prosthesis to allow tissue ingrowth and thus prevent tissue hardening. The polyurethane foams currently used, however, are known to biodegrade after implantation. Thus, a need exists for the development of a biostable tissue ingrowth platform which has improved cellula infiltration characteristics while simultaneously not being subject to extensive long term biodegradation.

The currently used medical polyurethanes are usually polyether-based polyurethanes in spite of studies which have shown that ether groups especially ethers in which the methyl group is in the alpha position to the ether oxygen is susceptible to in vivo oxidation. Oxidation occurs and causes eventual chain cleavage, leading to significant reductions in molecular weight at the surface and eventual surface fissuring. Polyurethanes made by using lower amounts of the ether component per weight of polymer have been shown to produce a polymer having increased biostability and exhibiting less surface fissuring after implantation for several months.

Biocompatible polyurethanes soluble in organic solvents are disclosed in Ger. Offen. DE 3, 643,465 (G. Wick, 1988). These polyurethanes are claimed to be compatible with blood and tissue and useful as catheters, prostheses, and in the production of pacemaker housings. The polyurethanes are produced by reacting an aliphatic or cycloaliphatic macrodiol with 3-33 molar proportion of a cycloaliphatic diisocyanate to give a pre-adduct having NCO groups followed by chain elongation of the pre-adduct with a mixture of the macrodiol and a specific lower aliphatic diol, i.e. trimethylhexanediol. The macrodiol may be 1, 6-hexanediolpolycarbonate carbonate. The resultant thermoplastic polymers have tensile strengths of about 4750–5200 psi, moduli of elasticity of about 300 psi or higher, and ultimate elongations of about 460–520%.

A thin abrasion-resistant polyurethane coating for transparent polycarbonate substates has been prepared by reaction of a polycarbonatediol with an aliphatic diisocyanate and then hardened with a trifunctional crosslinking agent. (Ger. Offen. DE 3,323,684)

Polyurethane elastomers for use a coating with superior durability have been prepared from a polyester polyol derived from 1,10- decanedicarboxylic acid and a polycarbonate polyol by reaction with polyisocyanates and optionally with chain extenders. (Japan Kokai 57/31919, 1982)

Polycarbonate diols have been used in the manufacture of polycarbonate-polyurethanes for bilayer safety glass automobile windshields by polymerization of an aliphatic diol with a dialkyl carbonate in the presence of an alkali metal-free titanium compound. (U.S. Pat No. 4,160,853)

There exists a substantial need for a family of biostable polyurethane polymers some members of which can be used to produce improved insulating compositions for pacemaker leads, small diameter vascular grafts, and tissue ingrowth platforms having improved cellular infiltration characteristics for mammary prostheses.

It is an object of the present invention to provide such polyurethanes, particularly polyurethanes which may be conventionally steam sterilized.

It is a further object to produce a biostable polyurethane having a tensile strength in excess of 4000 psi and an elastic modulus of less than about 200 psi.

SUMMARY OF THE INVENTION

The biostable polyurethanes of this invention are derived from organic diisocyanates and polycarbonate diols which are chain extended with diamines or mixtures of diamines and alkanolamines, or alkanolamines or with diols. When the polyurethane is used in the preparation of long-term internally implanted aritlces, it is preferred than aliphatic or cycloaliphatic diisocyanates be used. For other applications, aromatic diisocyanates and mixtures of aromatic and aliphatic and/or cycloaliphatic diisocyanates may be used.

Biostable polyurethanes which may be steam sterilized can be prepared from an isocyanate terminated prepolymer of an organic diisocyanate and a polycarbonate glycol, which prepolymer is chain extended with a diamine having about 2 to 10 carbon atoms.

Biostable polyurethanes can be prepared either via a one shot reaction of an organic diisocyanate, a polycarbonate glycol and a diol having about 2 to 8 carbon atoms or by preparing an isocyanate terminated prepolymer by reaction of an aliphatic or cycloaliphatic diisocyanate with a polycarbonate glycol and chain extending the prepolymer with a diol having about 2 to 8 carbon atoms.

The biostable polyurethanes of this invention can be used in the making of films and membrane and also various objects and articles which can be implanted within a living body such as pacemaker leads, pacemaker bodies, vascular grafts, mammary prostheses, probes, cannulas, catheters, artificial organs made from yarns of the invention polyurethanes and the like. It has been found that polyurethanes of the invention are biostable and compatible with tissue and blood; have excellent cellular infiltration characteristics when fashioned into porous structure, such as textile, microporous membrane, etc.; and are resistant to biodegradation. Additionally, the polyurethanes according to the invention have excellent mechanical properties.

DETAILED DESCRIPTION OF THE INVENTION

The present polyurethanes are the reaction products of an organic diisocyanate or mixtures of organic diisocyanates, a polycarbonate glycol and a diol, a diamine or mixtures of a diamine and are alkanolamine. When a diol is employed, either a one-shot or prepolymer technique can be used. In the case of diamines or mixtures of diamines and alkanolamines, either a one-shot or prepolymer technique may be used but a prepolymer technique is preferably utilized.

Diamine-extended polyurethanes have a relatively high urea linkage contents due to their diamine or diamine/alkanolamine extension. This high urea linkage content results in relatively high levels of hydrogen bonding which, in turn, produces strong elastic materials with good flex life properties. This high level of hydrogen bonding also renders the polyurethane pseudocrosslinked or pseudothermosetting.

Diol-extended polyurethanes have lower levels of hydrogen bonding which produces polymers having reduced physical properties, such as elongation, ultimate tensile strength, and flex life as compared to the equivalent diamine-extended counterparts. This low level of hydrogen bonding renders the diol extended polyurethane thermoplastic.

Formation of polyurethanes according to this invention includes reacting the —OH or hydroxyl groups of a polycarbonate glycol with the —NCO or isocyanate groups of an organic diisocyanate in an appropriate equivalent ratio of —NCO groups to —OH groups to form an isocyanate terminated moiety followed by chain extension with a diol, a diamine or a mixture of diamine and alkanolamine. The reactions are carried out in the presence of a suitable solvent and under appropriate reaction conditions, although non-solvent reactions can also be carried out.

The present polyurethanes can be based on a variety of diisocyanates where the diisocyanate may be represented by the formula OCN-R-NCO wherein R is aliphatic including groups such as aliphatic, aliphatic-alicyclic and aliphatic-aromatic hydrocarbon groups containing from about 4 to 26 carbon atoms, preferably from about 6 to 20 carbon atoms, more preferably from about 6 to 13 carbon atoms or an aromatic group preferably carbocyclic aryl or aralkyl having from about 6 to 14 carbon atoms. Representative examples of such diisocyanates include: tetramethylene diisocyanate, hexamethylene diisocyanate, trimethylhexamethylenediisocyanate, tetramethylxylylene diisocyanate, 4, 4-dicyclohexylmethane diisocyanate, dimer acid diisocyanate, isophorone diisocyanate, metaxylene diisocyanate, diethylbenzene diisocyanate, decamethylene 1, 10-diisocyanate, cyclohexylene 1, 2-diisocyanate and cyclohexylene 1, 4-diisocyanate, 2,4-toluene diisocyanate; 2,6-toluene diisocyanate; xylene diisocyanate; m-phenylene diisocyanate; hexahydrotolylene diisocyanate (and isomers), naphthylene-1,5-diisocyanate; 1-methoxyphenyl 2,4-diisocyanate diphenylmethane 4,4'-diisocyanate, 4,4'-biphenylene diisocyanate,3,3-dimethoxy-4,4-biphenyldiisocyanate;3,3-dimethyl 4,4' diisocyanate and mixtures thereof.

The polycarbonate glycols useful in making the present polyurethanes have molecular weight of from about 650 to 3500 molecular weight units' preferably 1000 to 2000 molecular weight units and have the following formula

OH[R$^1$-O(CO)O-R$^1$]$_n$OH in which R$^1$ is a linear chain of about 2 to 20 carbon atoms. A preferred polycarbonate glycol is hexanediolcarbonate glycol.

The diols chain extenders useful in the present invention have from about 2 to 8 carbon atoms which are preferably in a straight chain with no more than 2 side groups such as methyl or ethyl. The presence of more than two side groups, such as methyl or ethyl, is not desired since polyurethanes formed therefrom have lower tensile strengths. Exemplary of these diols are ethylene glycol, diethylene glycol, triethylene glycol, 1,4-butanediol, neopentyl glycol, 1,6-hexanediol, 1,8-octanediol, 1,2 and 1,3-propylene glycol, 2,3-butylene glycol, dipropylene glycol, dibutylene glycol and mixtures thereof.

Suitable aliphatic diamine chain extenders include diamines have about 2 to 10 carbon atoms. Exemplary diamines include ethylene diamine, propanediamines, butanediamine, pentanediamine, hexanediamine, heptanediamine, octanediamine, m-xylylene diamine, 1,4-diaminocyclohexane, 2-methylpentamethylene diamine and mixtures thereof. Suitable alkanolamine chain extenders include ethanolamine and the like.

The present polyurethanes can be prepared by reaction of the appropriate reactants in the presence or absence of an inert solvent, preferably under an inert atmosphere at a temperature of from about 60 to 150.C. Common solvents which may be used are typically polar organic solvents such as, for example, dimethylacetamide, dimethylformamide, tetrahydrofuran, cyclohexanone and 2-pyrrolidone. In polyurethanes which are chain extended with diol, the preferred equivalent ratio of NCO to hydroxyl of the polycarbonate glycol is from about 1.8 to 2.5 NCO per equivalent of hydroxyl. Approximately one equivalent of diol, diamine or diamine/alkanolamine mixture chain extender is used. In polyurethanes which are chain extended with diamine or a diamine/alkanolamine mixture, the preferred equivalent ratio of NCO to polycarbonate glycol hydroxyl is about 2.8 to 3.2 equivalents NCO to about 1.8 to 2 equivalents of hydroxyl.

When diamine or diamine/alkanolamine claim extension is employed a monofunctional amine chain control agent may be employed.

A conventional polyurethane catalysts such as organometallic compounds may be employed. Illustrative such catalysts are dibutyl tin dilaurate, dioctyl tin diluarate stannous octoate and zinc octoate.

The following examples illusrate typical preparations of polyurethanes embodying the present invention. These examples are illustrative and non-limiting.

EXAMPLE I

A four liter reactor equipped with continuous nitrogen blanketing and a heating mantel is charged with tetramethylxylylene diisocyanate (TMXDI) (2.1 equiv.), of 1,6-hexaneddiolcarbonate glycol having a molecular weight of 2000 (1.0 equiv.). The temperature is allowed to rise to 110° C. and 0.001% (based on the total weight) dioctyl tin dilaurate (Cotin 430 of Cosan Chemical Co.) is added. Agitation is begun and the mixture is allowed to react for three hours to form an isocyanate-terminated prepolymer. The prepolymer is then reacted with neopentyl diol (1.0 equiv.) at 110° C. for five hours.

The resultant thermoplastic polyurethane exhibits the following physical properties:

| | |
|---|---|
| Ultimate tensile strength | 6,100 psi |
| Ultimate elongation | 575% |
| Modulus at 100% strain | 300 psi |
| Hardness | 65 Shore A |
| Specific gravity | 1.01 |

The polyurethane is soluble in DMAc, DMF, THF, M-pyrrol, and methylene chloride. It is insoluble in alcohols, ketones, esters, and aliphatic hydrocarbons.

EXAMPLE II

The procedure of Example I is repeated except that the diisocyanate is replaced by 2.1 equiv. of 4,4-dicyclohexylmethane diisocyanate. The resultant thermoplastic polyurethane exhibits the following physical properties:

| | |
|---|---|
| Ultimate tensile strength | 6,400 psi |
| Ultimate elongation | 550% |
| Modulus at 100% strain | 310 psi |
| Hardness | 70 Shore A |
| Specific gravity | 1.01 |

EXAMPLE III

The procedure of example I is repeated except that the diisocyanate and the glycol react in the presence of 1000 ml of tetrahydrofuran and then the neopentyl diol is replaced by 2-methylpentamethylene polyurethane article according to diamine. The resultant thermoset polyurethane exhibits the following physical properties:

| | |
|---|---|
| Ultimate tensile strength | 4,100 psi |
| Ultimate elongation | 675% |
| Modulus at 100% strain | 125 psi |
| Hardness | 40 Shore A |
| Specific gravity | 0.35 |

EXAMPLE IV

The procedure of Example III is repeated except that the 2-methylpentamethylene diamine is replaced by ethylene diamine. The resultant thermoset polyurethane exhibits the following physical properties:

| | |
|---|---|
| Ultimate tensile strength | 4,600 psi |
| Ultimate elongation | 575% |
| Modulus at 100% strain | 150 psi |
| Hardness | 45 Shore A |
| Specific gravity | 0.35 |

EXAMPLE V

The procedure of Example II is repeated except that the neopentyl diol is replaced by hexane diol. The resultant thermoplastic polyurethane exhibits the following physical properties:

| | |
|---|---|
| Ultimate tensile strength | 6,100 psi |
| Ultimate elongation | 450% |
| Modulus at 100% strain | 475 psi |

We claim:

1. A biostable implantable polyurethane article having a low modulus of elasticity and a high ultimate tensile strength wherein said article is made from a polyurethane prepared by the reaction of tetramethylxylylene diisocyanate, metaxylene diisocyanate, an aliphatic or aliphatic-alicyclic organic diisocyanate or a mixture of said organic dissocyanates, a polycarbonate glycol wherein the polycarbonate glycol has the following formula:

in which $R^1$ is a linear hydrocarbon chain of about 2 to 20 carbon atoms said polycarbonate glycol having a molecular weight of from about 650 to 3500 molecular weight units and n having a value in accordance with the molecular weight units and n having a value in accordance with the molecular weight and an aliphatic diol having about 2 to 8 carbon atoms or an aliphatic diamine having about 2 to 10 carbon atoms or a mixture of an aliphatic diamine having about 2 to 10 carbon atoms and an alkanolamine, or alkanolamines said article having an ultimate tensile strength in excess of 4000 psi, an elastic modulus of 100% strain of between about 125 psi and 475 psi and a Shore A hardness of about 70 or less.

2. A biostable polyurethane article according to claim 1, in which the aliphatic diol having about 2 to 8 carbon atoms has no more than 2 side groups.

3. A biostable polyurethane article according to claim 1, wherein the organic diisocyanate is represented by the formula

OCN—R—NCO wherein R is an aliphatic group in which the aliphatic group contains from about 4 to 26 carbon atoms.

4. A biostable polyurethane article according to claim 1, wherein the diisocyanate is tetramethylene diisocyanate; hexamethylene diisocyanate; trimethyl-hexamethylene diisocyanate; tetramethylxylylene diisocyanate; 4, 4'-dicychohexylmethane diisocyanate; dimer acid diisocyanate; isophorone diisocyanate; metaxylene diisocyanate; decamethylene 1, 10-diisocyanate; cyclohexylene 1, 2-diisocyanate; cyclohexylene 1,4-diisocyanate; hexahydrotolylene diisoctanate (and isomers); and mixtures thereof.

5. A biostable polyurethane article according to claim 1, wherein the aliphatic diol is ethylene glycol, diethylene glycol, trimethylene glycol, 1, 4butanediol, neopentyl glycol, 1, 6-hexanediol, 1, 8-octanediol, 1, 2 or 1, 3-propylene glycol, 2, 3-butylene glycol, diproperylene glycol, dibutylene glycol or mixture thereof.

6. A biostable polyurethane article according a claim 1, wherein the aliphatic diamine is ethylene diamine, propanediamine, butanediamine, pentanediamine, hexanediamine, heptanediamine, octanediamine, m-xylylene diamine, 1, 4-diaminocyclohexane, 2-methylpentmethylene diamine or mixtures thereof.

7. A biostable polyurethane article according to claim 1, where the alkanolamine is ethanolamine.

8. A biostable polyurethane article according to claim 1, wherein the elastic modulus at 100% strain is less than 310 psi.

9. A biostable polyurethane article according to claim 1, wherein the elastic modulus at 100% strain is less than 200 psi.

10. A biostable polyurethane article according the claim 1, wherein said article is a vascular graft, a mammary prosthesis, a pacemaker lead, a pacemaker body, a probe, a cannula or a catheter.

11. A biostable polyurethane article according to claim 8, wherein said article is a vascular graft, a mammary prosthesis, a pacemaker lead, a pacemaker body, a probe, a cannula or a catheter as in claim 10.

12. A polystable polyurethane article according to claim 9, wherein said article is a vascular graft, a mammary prosthesis, a pacemaker lead, a pacemaker body, a probe, a cannula or a catheter as in claim 10.

13. A biostable implantable polyurethane article wherein said article is made from a polyurethane prepared by the reaction of an organic diisocyanate selected from the group consisting of tetramethylene diisocyanate, hexamethylene diisocyanate, trimethylhexamethylene diisocyanate, tetramethylxylylene diisocyanate, 4, 4-dicyclohexylmethane diisocyanate, dimer acid diisocyanate, isophorone diisocyanate, metaxylene diisocyanate, decamethylene 1, 10-diisocyanate, cyclohexylene 1, 2-diisocyanate, cyclohexylene 1, 4-diisocyanate, hexahydrotolylene diisocyanate (and isomers), and mixtures thereof, a polycarbonate glycol wherein the polycarbonate glycol has the following formula:

[HO[R$^1$-O(CO)O-R$^1$]$_n$OH]

[HOR$^1$]O(CO)O-R$^1$]$_n$ OH in which R$^1$ is a linear hydrocarbon chain of about 2 to 20 carbon atoms said polycarbonate glycol having a molecular weight of from about 650 to 3500 molecular weight units and n having a value in accordance with the molecular weight and an aliphatic diol having about 2 to [carbon atoms or an aliphatic diamine having about 2 to 10 carbon atoms and an alkanolamine, or alkanolamines said article having an ultimate tensile strength in excess of 4000 psi, an elastic modulus at 100% strain of between about 125 psi and 475 psi and a Shore A hardness of about 70 or less.

14. A biostable polyurethane article according to claim 13, in which the alphatic diol having about 2 to 8 carbon atoms has no more than 2 side groups.

15. A biostable polyurethane article according to claim 13, wherein the aliphatic diol is ethylene glycol, diethylene glycol, trimethylene glycol, 1, 4-butanediol, neopentyl glycol, 1, 6-hexanediol, 1, 8-octanediol, 1, 2 or 1, 3-propylene glycol, 2, 3-butylene glycol, dipropylene glycol, dibutylene glycol or mixtures thereof.

16. A biostable polyurethane article according to claim 13, wherein the aliphatic diamine is ethylene diamine, propanediamine, butanediamine, pentanediamine, hexanediamine, heptanediamine, octanediamine, m-xylylene diamine, 1, 4-diaminocyclohexane, 2-methylpentamethylene diamine or mixtures thereof.

17. A biostable polyurethane article according to claim 13, wherein the alkanolamine is ethanolamine.

18. A biostable polyurethane article according to claim 13, wherein the elastic modulus at 100% strain is less than 310 psi.

19. A biostable polyurethane article according to claim 13, wherein the elastic modulus at 100% strain is less than 200 psi.

20. A biostable implantable polyurethane article wherein said article is made from a polyurethane prepared by the reaction of an organic diisocyanate selected from the group consisting of tetramethylene diisocyanate, hexamethylene diisocyanate, trimethyl-hexamethylenediisocyanate, tetramethylxylylene diisocyanate, 4, 4- dicyclohexylmethane diisocyanate, dimer acid diisocyanate, isophorone diisocyanate, metaxylene diisocyanate, decamethylene 1, 10-diisocyanate, cyclohexylene 1, 2-diisocyanate, cyclohexylene 1, 4-diisocyanate, hexahydrotolylene diisocyanate (and isomers), and mixtures thereof, a polycarbonate glycol wherein the polycarbonate glycol has the following formula:

[HO[R$^1$-O(CO)O-R$^1$]$_n$OH]

HOR$^1$[O(CO)O-R$^1$]$_n$OH in which R$^1$ is a linear hydrocarbon chain of about 2 to 20 carbon atoms said polycarbonate glycol having a molecular weight of from about 650 to 3500 molecular weight units and n having a value in accordance with the molecular weight and an aliphatic diol wherein the aliphatic diol is selected from the group consisting of ethylene glycol, diethylene glycol, trimethylene glycol, 1, 4-butanediol, neopentyl glycol, 1, 6-hexanediol, 1, 8-octanediol, 1, 2 or 1, 3-propylene glycol, 2, 3-butylene glycol, dipropylene glycol, dibutylene glycol and mixtures thereof, or an aliphatic diamine wherein the aliphatic diamine is selected from the group consisting of ethylene diamine, propanediamine, butanediamine, pentanediamine, hexanediamine, heptanediamine, octanediamine, m-xylylene diamine, 1, 4-diaminocyclohexane, 2-methylpentamethylene diamine and mixtures thereof, or a mixture of said aliphatic diamine and an alkanolamine, or alkanolamines said article having an ultimate tensile strength in excess of 4000 psi and an elastic modulus at 100% strain of between about 125 psi and 475 psi.

21. A biostable polyurethane article according to claim 20, wherein the elastic modulus at 100% strain is less than 310 psi.

22. A biostble polyurethane article according to claim 20, wherein the elastic modulus at 100% strain is less than 200 psi.

23. A biostable polyurethane article according to claim 1, wherein the Shore A hardness is between about 45 and 70.

24. A biostable polyurethane article according to claim 13, wherein the Shore A hardness is between about 45 and 70.

25. A biostable polyurethane article according to claim 20, wherein the Shore A hardness is between about 45 and 70.

* * * * *